United States Patent [19]

Yamada et al.

[11] 4,312,945

[45] Jan. 26, 1982

[54] METHOD AND APPARATUS OF MEASURING THE SPECIFIC ACTIVITY OF DEHYDROGENASES IN TISSUE

[75] Inventors: Masaoki Yamada, Tokushima; Kenji Onogi; Ryozo Ito, both of Yokohama, all of Japan

[73] Assignee: Nippon Kogaku K.K., Tokyo, Japan

[21] Appl. No.: 197,618

[22] Filed: Oct. 16, 1980

Related U.S. Application Data

[63] Continuation of Ser. No. 84,749, Oct. 15, 1979, abandoned.

[30] Foreign Application Priority Data

Oct. 19, 1978 [JP] Japan ................................. 53-128923

[51] Int. Cl.³ ............................................. C12Q 1/32
[52] U.S. Cl. ..................................... 435/26; 435/291; 435/808; 422/68
[58] Field of Search ..................... 422/68, 73; 435/26, 435/291, 808

[56] References Cited

PUBLICATIONS

Wallace, T. C. et al., "Assay of Enzymatic Activity by Electrochemical Detection of Reduced Coenzyme", Analytical Biochem., vol. 80, pp. 133-144 (1977).

Allain, C. C. et al., "Rapid Single-Step Kinetic Colorimetric Assay for Lactate Dehydrogenese in Serum", Clinical Chemistry, vol. 19 (2), pp. 223-227 (1973).

*Primary Examiner*—Benoît Castel
*Attorney, Agent, or Firm*—Fitzpatrick, Cella, Harper & Scinto

[57] ABSTRACT

In a method of measuring the specific activity of dehydrogenases by using a specimen prepared through a first procedure of causing dehydrogenases in tissue flake to be measured to be reacted with a substrate for a predetermined time and dyeing the same with tetrazolium salt and a second procedure of dyeing the protein in the flake with naphthol yellows, there is provided a third procedure of washing the enzyme-dyed flake with alcohol for a predetermined time after the first procedure. A specimen prepared through the first, second and third procedures is is microphotometered by the use of three predetermined wavelengths in the vicinity of 450 nm, 570 nm and 700 nm, and the specific activity of the dehydrogenases is measured from data obtained corresponding to the respective wavelengths.

9 Claims, 19 Drawing Figures

METHOD AND APPARATUS OF MEASURING THE SPECIFIC ACTIVITY OF DEHYDROGENASES IN TISSUE

This is a continuation of application Ser. No. 84,749, filed Oct. 15, 1979, now abandoned.

BACKGROUND OF THE INVENTION

1. Field of the Invention

This invention relates to a method of measuring the specific activity of dehydrogenases in tissue and to an apparatus for carrying out the same.

2. Description of the Prior Art

Chiefly in the field of biochemistry, it has heretofore been practiced to determine the enzyme activity of tissue. According to this measuring method, the entire tissue is triturated and an object component is extracted by centrifugal separation or the like, whereafter enzyme activity is measured by colorimeteric method. However, in such biochemical measurement, the tissue is triturated and it is therefore impossible to know the localization of enzyme in the tissue and moreover, it is not possible to completely separate the object component alone and thus, such measurement has been inferior in accuracy. On the other hand, the field of enzyme tissue chemistry has developed which is aimed at knowing in what region of the tissue how much object component is contained. In this field, a method is adopted which comprises causing the enzyme of tissue cells to act on enzyme substrate under predetermined conditions, decomposing the substrate by the action of the enzyme, capturing the decomposition product as a reacting substance at the part of action, and visualizing it by a reagent. In such measuring method, however, the judgment that the enzyme activity is strong or weak has been visually empirically made by the measurer and therefore, the result of the measurement has been very subjective and this has led to a disadvantage that the determination is impossible. That is, the measuring methods in the fields of biochemistry and enzyme tissue chemistry have their own merits and demerits in measuring the enzyme activity in tissue and in these methods, it has been difficult to determine the enzyme activity and at the same time, know the localization of enzyme in tissue.

SUMMARY OF THE INVENTION

It is a first object of the present invention to provide an entirely novel method which enables one to know the localization of dehydrogenases in tissue and to accurately determine the dehydrogenases activity.

It is a second object of the present invention to provide an apparatus for carrying out such novel method.

The invention will become fully apparent from the following detailed description thereof taken in conjunction with the accompanying drawings.

DESCRIPTION OF THE PREFERRED EMBODIMENTS

A specimen of tissue flake used with the present invention is prepared by procedures (a)–(f) described hereinafter.

(a) An object tissue is frozen, whereafter a flake is cut out therefrom and sticked on cover glass.

(b) By using tetrazolium salt as the hydrogen receiver, the flake is reacted with a substrate mixed liquid selected in accordance with the dehydrogenases to be measured. This procedure is usually called the enzyme dyeing.

Figure 1:
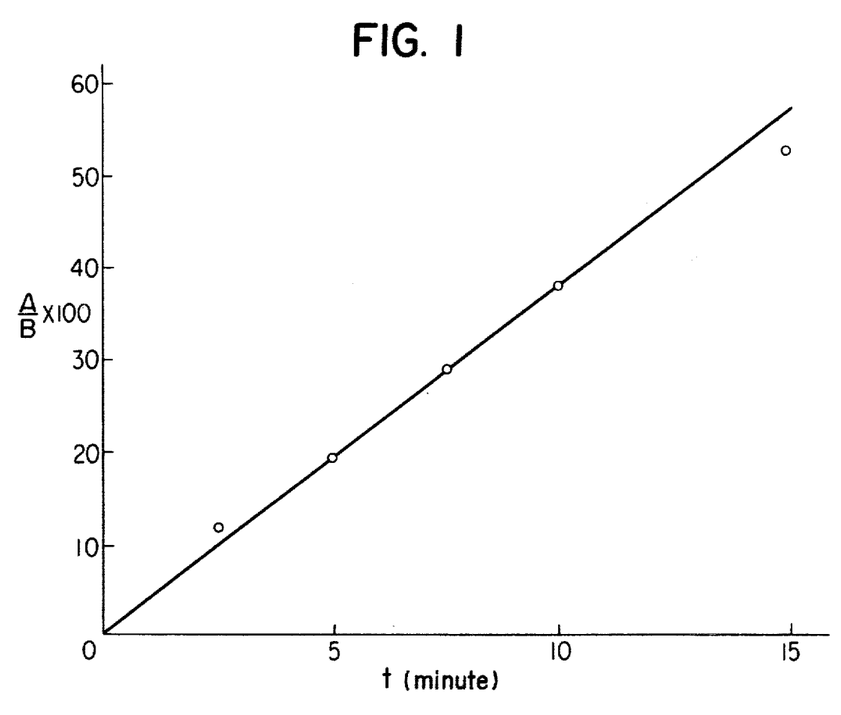
FIG. 1 shows the relation between the reaction time and the decomposed amount of the substrate when L-lactate:NAD oxidoreductase is selected as the object of photometry.
Figure 2:
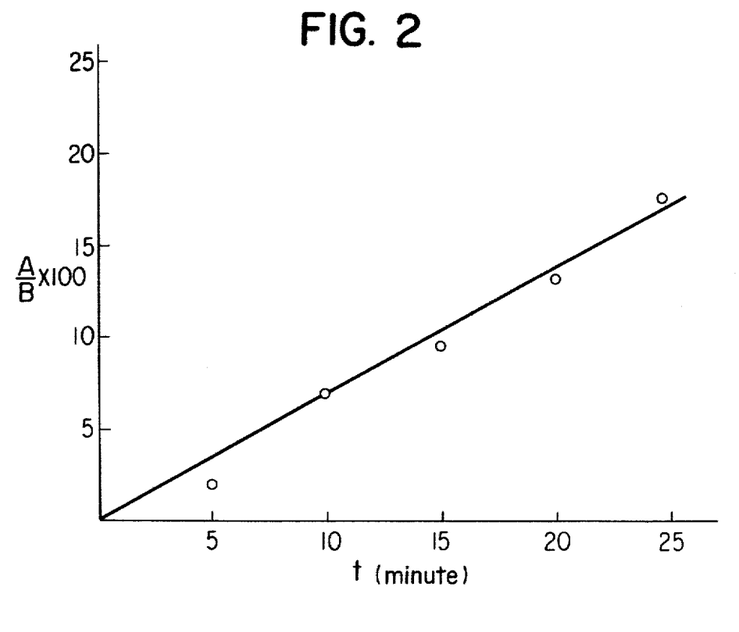
FIG. 2 shows the relation between the reaction time and the decomposed amount of the substrate when L-malate:NAD oxidoreductase is selected as the object of photometry.

(c) A predetermined time after the flake has been reacted at about 37° C., it is fixed by formalin or the like, thereby stopping the enzyme reaction. This predetermined time is predetermined for each enzyme and for example, it is designated to 15 minutes or less for L-lactate:NAD oxidoreductase, and to 25 minutes or less for L-malate:NAD oxidoreductase. This is for the reason set for below. The relation between the reaction time and the decomposed amount of the substrate when L-lactate:NAD oxidoreductase is selected as an object of photometry is shown in FIG. 1. In FIG. 1, the abscissa represents the reaction time t after the enzyme and the substrate were mixed together, and the ordinate expresses the amount (A) of substrate decomposed by L-lactate:NAD oxidoreductase to equalize the amount of protein which differs from a photometered region to another, as the ratio thereof to the amount (B) of protein in the same photometered region, in order to show the decomposed amount of the substrate. As is clear from FIG. 1, when a substrate is added to L-lactate:-NAD oxidoreductase, the decomposition product by enzyme is substantially linearly increased within 15 minutes. Therefore, if the reaction of L-lactate:-NAD oxidoreductase is stopped within 15 minutes after the substrate has been added, enzyme activity can be determined. FIG. 2 is a graph similar to FIG. 2 but showing the case where L-malate:NAD oxidoreductase is selected as the object of photometry. The decomposition speed of the substrate by L-malate:NAD oxidoreductase is about one-fourth of the decomposition speed of the substrate by L-lactate:NAD oxidoreductase, but it is seen that within 25 minutes, the decomposition product by enzyme is substantially linearly increased. It is therefore seen that to determine dehydrogenases activity, the reaction may be stopped within 25 minutes after the substrate has been added. In this manner, each dehydrogenases differs in progress of reaction after the substrate has been added, but it is possible to determine a fixed time suitable for each enzyme by previously obtaining the characteristic as shown in FIG. 1 or 2.

(d) The flake is washed with alcohol. The time during which the flake is washed with alcohol is about 10 minutes for succinic dehydrogenase, and about 3 minutes for other dehydrogenases such as L-lactate:NAD oxidoreductase and L-malate-NAD oxidoreductase. For the washing, monatomic alcohol such as ethanol may conveniently be used because it is readily available and easy to handle.

(e) The flake is washed with water, whereafter the protein in the flake is dyed with naphthol yellows. This procedure is usually called the protein dyeing.

(f) The flake is washed, whereafter it is enveloped in liquid paraffin.

Figure 3:
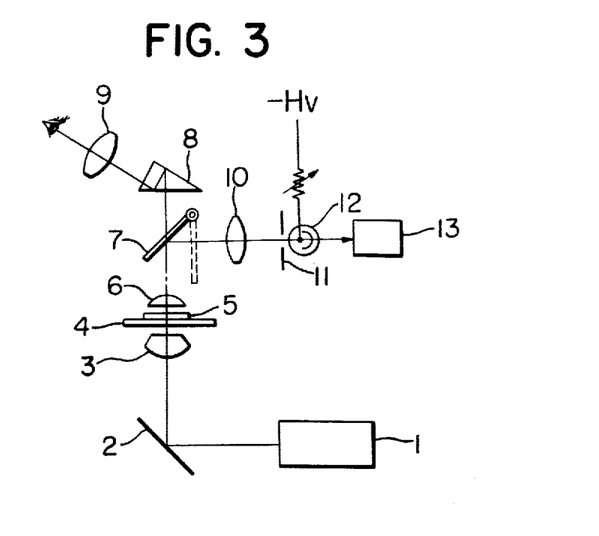
FIG. 3 shows an apparatus for spectrophotometrically measuring a specimen.

The specimen thus prepared can be spectrophotometrically measured by a well-known microphotometer device as shown in FIG. 3. In FIG. 3, a monochrometer 1 may emit a light beam of any wavelength. The light beam from the monochrometer 1 reflected by a mirror 2 is condensed on the specimen 5 on a stage 4 by a condenser lens 3. The light beam passed through the specimen 5 is passed through an objective lens 6, whereafter it is selected toward a view field optical system and a metering optical system by a change-over mirror 7. When the change-over mirror 7 is in a first position indicated by dotted line, the light beam passed through the objective lens 6 is directed to an eyepiece 9 by a prism 8, so that the measurer can observe the specimen through the eyepiece 9. When the change-over mirror 7 is in a second position indicated by solid line, the light beam passed through the objective lens 6 is reflected by the change-over mirror 7, whereafter it is condensed on an image plane diaphragm 11 by a condenser lens 10. A photoelectric converter 12 photoelectrically converts the light beam passed through the image plane diaphragm 11. The photoelectrically converted signal is converted into a light absorption degree or the like by an operational circuit 13. With such a construction, the change-over mirror 7 may be microscopically examined in the first position and the position of the specimen 5 to be metered may be determined, whereafter the change-over mirror 7 may be changed over to the second position, thereby effecting microspectrophotometry.

Figure 4:
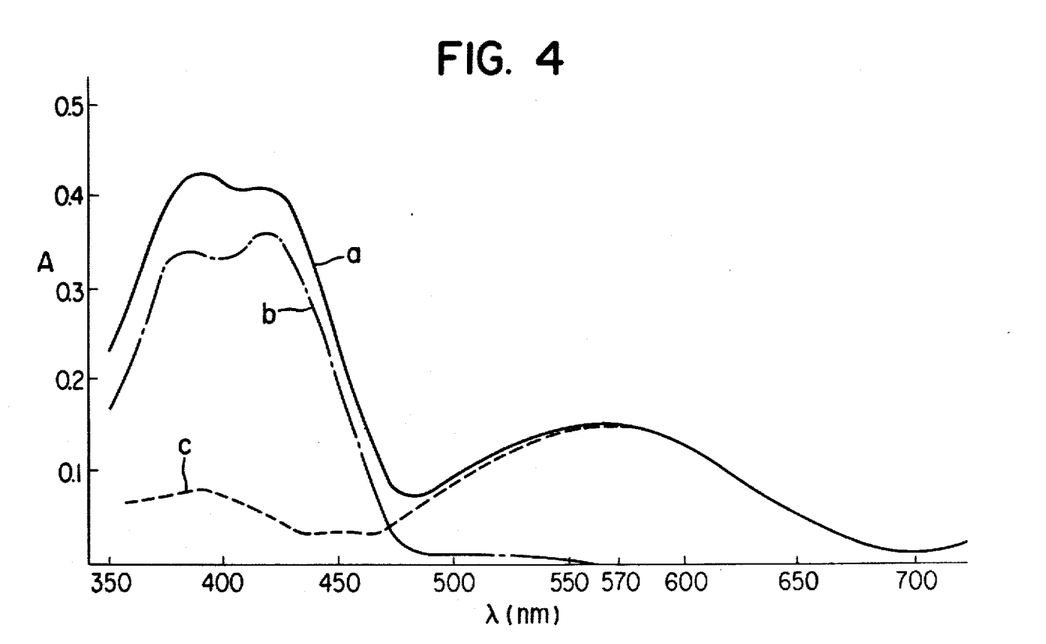
FIG. 4 shows the absorption spectral curve (a) of a specimen obtained by the conventional method, the absorption spectral curve (b) when protein was dyed with naphthol yellows, and the absorption spectral curve (c) of a specimen which was obtained by adding a substrate to the same dehydrogenases as the enzyme to be measured and dyeing it with tetrazolium salt.

Next, the meaning of the procedure (d) which is a feature of the present invention will be described by comparing the absorption spectral curve obtained by spectrophotometering a specimen prepared by carrying out the procedure (d). In the above-mentioned specimen preparation procedures, if a specimen prepared without carrying out the procedure (d) is spectrophotometered, there is obtained the absorption spectral curve as shown by curve (a) in FIG. 4, for example. In the absorption spectral curve of FIG. 4, the abscissa represents wavelength λ and the ordinate represents the light absorption degree A. However, the metering data of FIG. 4 has been obtained by stopping the reaction in a predetermined time after enzyme reaction has been started, as mentioned in the procedure (b) above, said predetermined time differing between the individual dehydrogenases to be measured. The curve (b) in FIG. 4 is the absorption spectral curve when protein was dyed with naphthol yellows, and the curve (c) in FIG. 4 is the absorption spectral curve when a substrate was added to the same dehydrogenase as the enzyme in the flake which is to be measured and the mixture was dyed with tetrazolium salt. As can be seen from the curve (b) in FIG. 4, the absorption spectral curve when protein was dyed with naphthol yellows has a tendency that there is maximum absorption in the vicinity of wavelength 390 nm and 430 nm and absorption becomes substantially null in the vicinity of wavelength 560 nm or more. Also, as can be seen from the curve (c), the absorption spectral curve when a substrate was added to dehydrogenases and the mixture was dyed with tetrazolium salt has a tendency that there is a portion in which absorption is small in the vicinity of wavelength 450 nm and minimum absorption in the vicinity of wavelength 700 nm and there is maximum absorption in the vicinity of wavelength 580 nm. The tendency of the curve (c) is commonly obtained for all dehydrogenases. The addition of the curves (b) and (c) is the curve (a).

Figure 5:
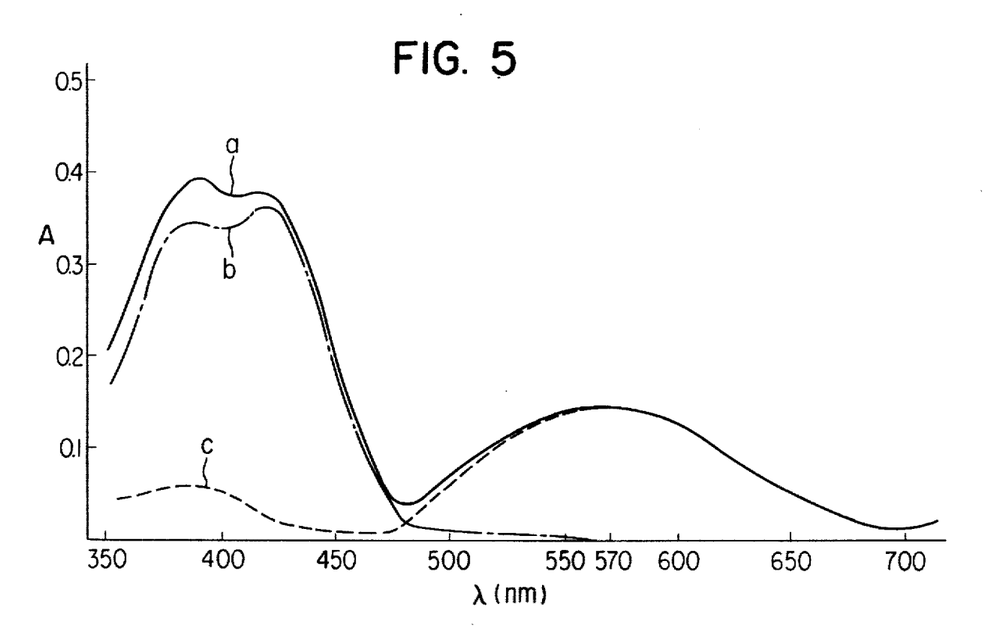
FIG. 5 shows the absorption spectral curve (a) of an alcohol-washed specimen, the absorption spectral curve (b) when protein was dyed with naphthol yellows, and the absorption spectral curve (c) of a specimen which was obtained by adding a substrate to the same dehydrogenases as the enzyme to be measured and dyeing it with tetrazolium salt, thereafter washing the same.

On the other hand, if a specimen subjected to the procedure (d) in the specimen preparation process is spetrophotometered, there is obtained the absorption spectral curve as shown by the curve (a) in FIG. 5. The curve (b) in FIG. 5 is the absorption spectral curve when protein way dyed with naphthol yellows, and it is entirely equal to the curve (b) in FIG. 4. The curve (c) in FIG. 5 is the absorption spectral curve when a substrate was added to the same dehydrogenase as the enzyme in the flake to be measured and the mixture was dyed with tetrazolium salt, whereafter it was washed with alcohol for a time equal to the washing time of the procedure (d) imparted to the flake. As can be seen from the comparison between the curve (c) of FIG. 4 and the curve (c) of FIG. 5, if a substrate is added to dehydrogenases and the mixture is dyed and thereafter washed with alcohol, the portion in which absorption is small in the vicinity of wavelength 450 nm of the absorption spectral curve is reduced in level. Therefore, if the flake is washed with alcohol for the predetermined time examined for each enzyme as mentioned in the procedure (d), it is possible to equalize the light absorption degree of minimum absorption in the vicinity of wavelength 700 nm to the light absorption degree in the vicinity of wavelength 450 nm. In FIG. 5, the light absorption degree at wavelength 450 nm of the curve (a) is equal to the sum of the light absorption degree of the curve (b) at wavelength 450 nm and the light absorption degree of the curve (c) at wavelength 450 nm. Also, the light absorption degree of the curve (c) at wavelength 450 nm is equal to the light absorption degree of the curve (a) at wavelength 700 nm. Therefore, if the light absorption degree of the curve (a) at wavelength 700 nm is subtracted from the light absorption degree of the curve (a) at wavelength 450 nm, there is obtained the light absorption degree of the curve (b) at wavelength 450 nm and this can be regarded as the light absorption degree which depends only on the protein contained in the region of the specimen which has been metered. Also, since the absorption of protein is zero at wavelength 570 nm, the light absorption degree of the curve (a) at wavelength 570 nm can be regarded as the light absorption degree which provides the standard of the amount of enzyme contained in the region of the specimen which has been metered. Therefore, if the specimen prepared through the aforementioned procedures (a)-(f) is metered at wavelengths 450 nm, 570 nm and 700 nm and the following equation (1).

$$I_{570}/(I_{450}-I_{700}) \qquad (1)$$

is operated between the light absorption degrees $I_{450}$, $I_{570}$ and $I_{700}$ obtained at the respective wavelengths, then there may be obtained the enzyme specific activity which represents the amount of enzyme per unit amount of protein in the metered region. The enzyme specific activity is a value which has nothing to do with the thickness of the specimen in the metered region and may therefore be regarded as the standard of the amount of enzyme.

Figure 6:
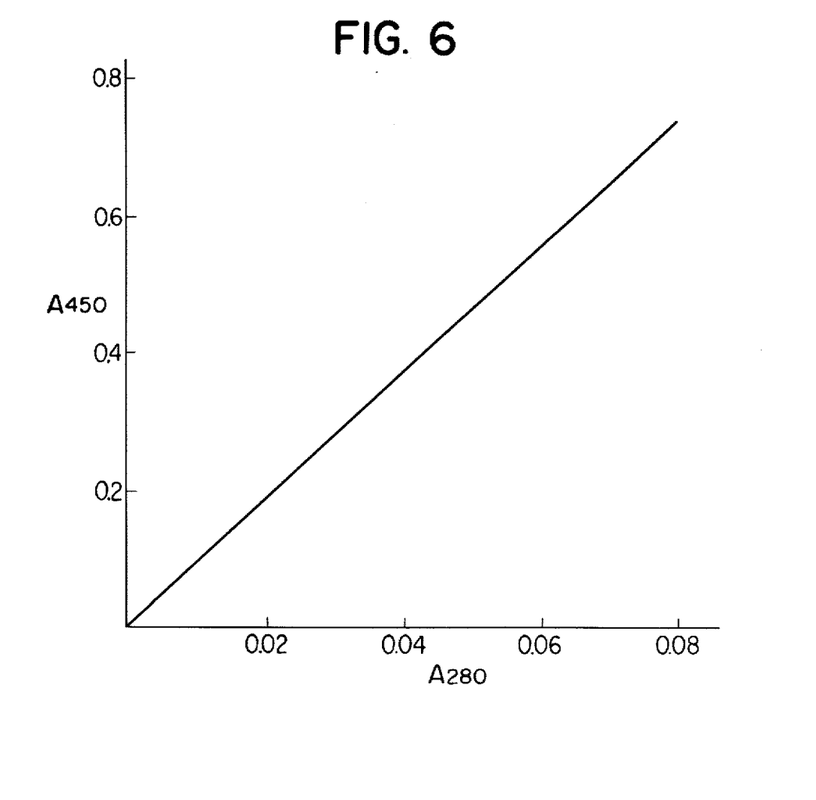
FIG. 6 shows the relation between the light absorption degree $A_{280}$ of a thin layer model at the absorption wavelength 280 nm commonly used as the parameter of density of undyed protein and the light absorption degree $A_{450}$ at the absorption wavelength 450 nm when protein is dyed with naphthol yellows.

The amount of enzyme in the metered region of the specimen can be known by seeking after the amount of protein from the light absorption degree at wavelenth 450 nm when protein is dyed with naphthol yellows and multiplying this amount of protein by the above-mentioned enzyme specific activity. FIG. 6 shows the relation between the light absorption degree $A_{280}$ of a thin layer model at the absorption wavelength 280 nm commonly used as the parameter of the density of undyed protein and the light absorption degree $A_{450}$ at the absorption wavelength 450 nm when protein is dyed with naphthol yellows and as is apparent from this Figure, a linear relation is established between the two. Therefore, by seeking after the light absorption degree at a corresponding wavelength 280 nm from the light absorption degree at wavelength 450 nm, the amount of protein in the metered region can be known from the value of that light absorption degree. Accordingly, the amount of enzyme can be known by the above-described operation.

Reference is now had to FIGS. 7, 8, 9 and 10 to describe an apparatus for carrying out the method of the present invention which has become apparent from the foregoing description and the operation of such apparatus.

Figure 7:
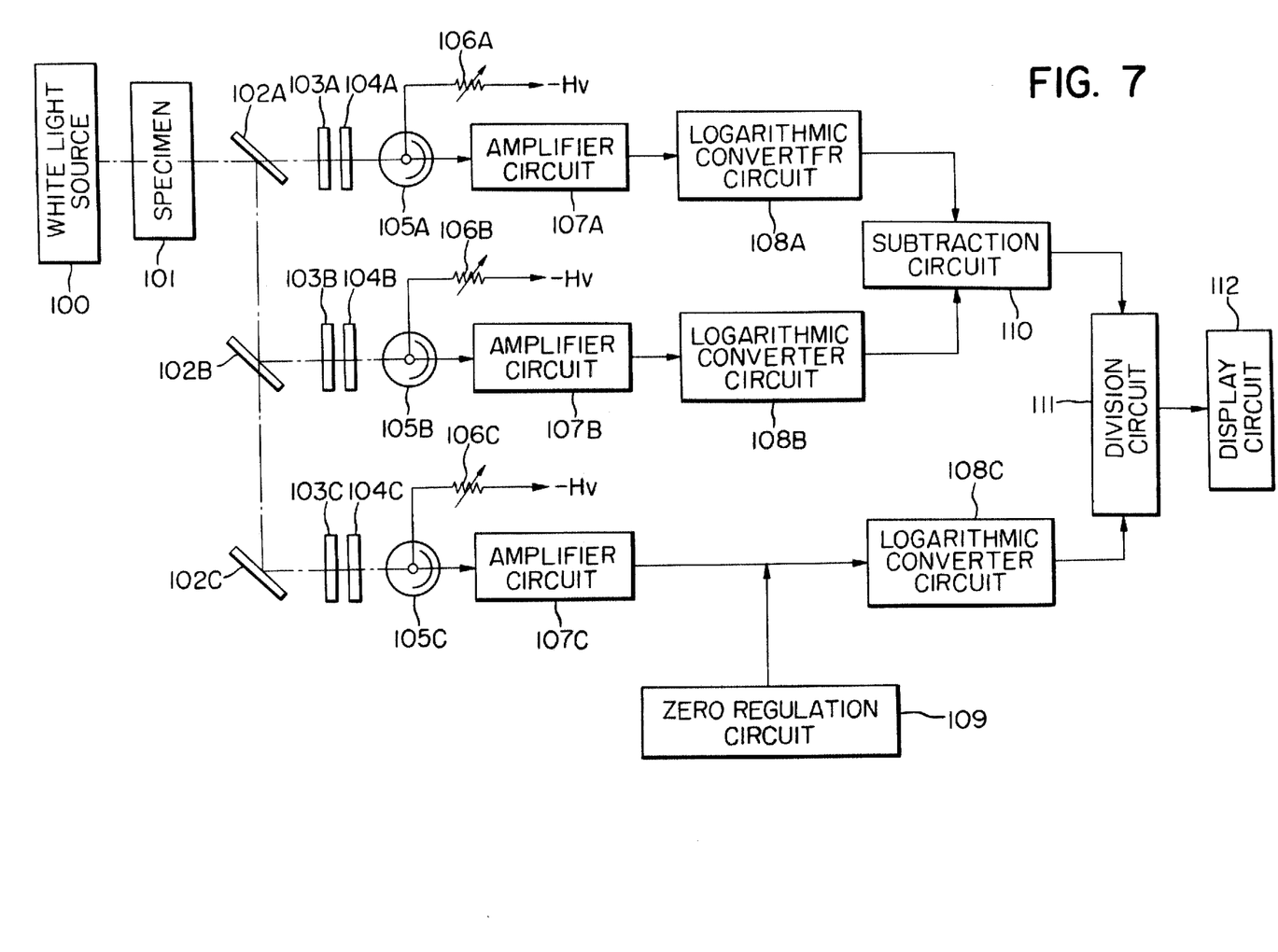
FIG. 7 shows an embodiment of the apparatus according to the present invention.

In FIG. 7, the light beam from a white light source 100 passes through a specimen 101 prepared through the aforementioned procedures (a)-(f) and is separated by a half-mirror 102A. The light passed through the half-mirror 102A passes through a filter 103A which passes therethrough only a light beam in the vicinity of wavelength 450 nm and a variable density filter (hereinafter referred to as the ND filter) 104A to a photomultiplier 105A, by which the light is photoelectrically converted. The photomultiplier 105A has its sensitivity adjustable by changing a resistor 106A. The light reflected by the half-mirror 102A is split by a half-mirror 102B. The light reflected by the half-mirror 102B passes through a filter 103B which passes therethrough only a light beam in the vicinity of wavelength 700 nm and ND filter 104B to a photomultiplier 105B, by which the light is photoelectrically converted. The photomultiplier 105B, like the photomultiplier 105A, has its sensitivity adjustable by changing a resistor 106B. The light passed through the half-mirror 102B is reflected by a mirror 102C and passes through a filter 103C which passes therethrough only a light beam in the vicinity of wavelength 570 nm and ND filter 104C to a photomultiplier 105C, by which the light is photoelectrically converted. The photomultiplier 105C also has its sensitivity adjustable by changing a resistor 106C. In FIG. 7, the lens systems between the light source 100 and the photomultipliers 105A, 105B, 105C are not shown, but these lens systems can be easily thought out by those skilled in the art from the known technique (see FIG. 3). The photoelectric conversion signals of the photomultipliers 105A, 105B and 105C are respectively amplified by amplifier circuits 107A, 107B and 107C, whereafter they are logarithmically converted by logarithmic converter circuits 108A, 108B and 108C, respectively. A zero regulation circuit 109 is connected between the amplifier circuit 107C and the logarithmic converter circuit 108C to remove the dark current of the photomultiplier 105C.

A subtraction circuit 110 subtracts the output of the logarithmic converter circuit 108B from the output of the logarithmic converter circuit 108A. A division circuit 111 divides the output of the logarithmic converter circuit 108C by the output of the subtraction circuit 110. A display circuit 112 effects the display corresponding to the output of the division circuit 111.

The operations of the apparatus shown in FIG. 7 will be described in succession starting from the stage of adjustment.

Figure 8A:
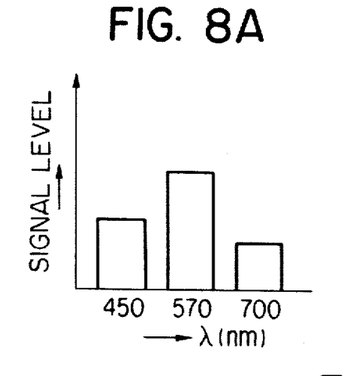
FIGS. 8A, 8B and 8C illustrate the initial setting operation in the apparatus of FIG. 7.
Figure 8B:
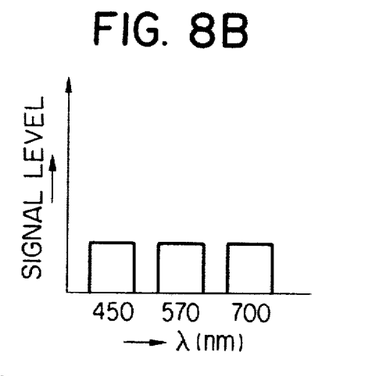
Figure 8C:
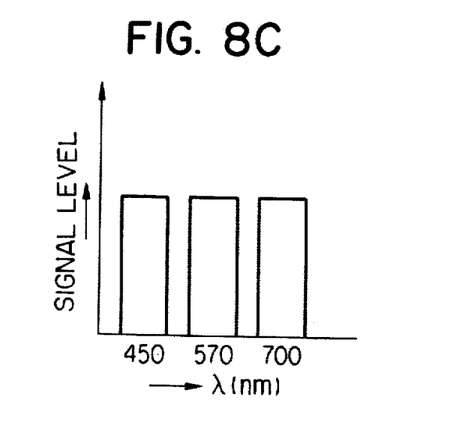

First, a case is considered where the specimen 101 is removed from the light path and the transmittivities of the ND filters 104A, 104B and 104C are equal and the sensitivities of the photomultipliers 105A, 105B and 105C are set to substantially equal levels. Due to the characteristic of the light source 100 and the spectral sensitivity characteristics of the photomultipliers, the outputs of the photomultipliers differ in level of each wavelength as shown in FIG. 9A. However, the transmittivity, the light absorption degree, etc. are sought after with the values in the absence of the specimen as the standard and therefore, if the levels of signals for the respective wavelengths in the absence of the speciment differ, S/N will differ and the circuit construction will become complicated. Therefore, in the construction according to an embodiment of the present invention, the ND filters 104A, 104B and 104C are inserted in the light path and the photoelectric outputs of the photomultipliers 105A, 105B and 105C are preadjusted to the lowest output level as shown in FIG. 8B (the level of 700 nm in the case of the shown example). In the case of the shown example, the ND filter 104B is unnecessary. Thereafter, the sensitivities of the photomultipliers 105A, 105B and 105C sre varied by changing the values of the resistors 106A, 106B and 106C and adjustment is effected such that the photoelectric outputs respectively assume the standard levels as shown in FIG. 8C. The logarithmic converter circuits 108A, 108B and 108C are set such that the level set as shown in FIG. 8C is converted into zero light absorption degree and the other levels are converted into corresponding light absorption degrees. On the other hand, the output of the amplifier circuit 107C is pre-cancelled by the zero regulation circuit 109 so that, when there is no light incident on the photomultiplier 105C, the input of the logarithmic converter circuit 108C becomes zero. This is a known technique.

After the above-described preparation for measurement has been completed, the specimen is inserted in the light path. The light beam from the light source 100 is condensed on an appropriate region of the speciment 101 by the known micro-spectrophotometric optical system as shown in FIG. 3, and of the light passed through said region, light beams of wavelengths 450 nm, 570 nm and 700 nm are photoelectrically converted by the photomultipliers 105A, 105C and 105B. The photoelectrical signals are amplified by the amplifier circuits, and thereafter applied to the logarithmic converter circuit 108A, 108B and 108C. The logarithmic converter circuits 108A, 108B and 108C respectively put out signals $I'_{450}$, $I'_{700}$ and $I'_{570}$ which are logarithmic conversions of the input signals. The reason why the outputs of the logarithmic converter 108A and 108B are $I'_{450}$ and $I'_{700}$ is that these two outputs contain a common error $\alpha$ resulting from the dark current or the like. (However, it is to be understood that the characteristics of the photomultipliers, etc. are equal.) Accordingly, if the values corresponding to the light absorption degrees are determined as $I_{450}$ and $I_{700}$, respectively, $I_{450} = I'_{450} - \alpha$ and $I_{700} = I'_{700} - \alpha$. The output of the subtraction circuit 110 becomes $I_{450} - I_{700}$ and the error $\alpha$ is cancelled here. The division circuit 111 effects the operation $$I_{570}/(I_{450} - I_{700})$$

shown by equation (1) and thus, the enzyme specific activity is displayed on the display circuit 112.

The half-mirror 102A used in the above-described embodiment may be replaced with a dichroic mirror which passes therethrough only a light beam in the vicinity of wavelength 450 nm, and the half-mirrors 102B and 102C may be replaced with dichroic mirrors which pass therethrough only light beams in the vicinity of wavelengths 700 nm and 570 nm. In this case, the efficiency of signals may be enhanced as compared with the case where the half-mirrors are used.

Figure 9:
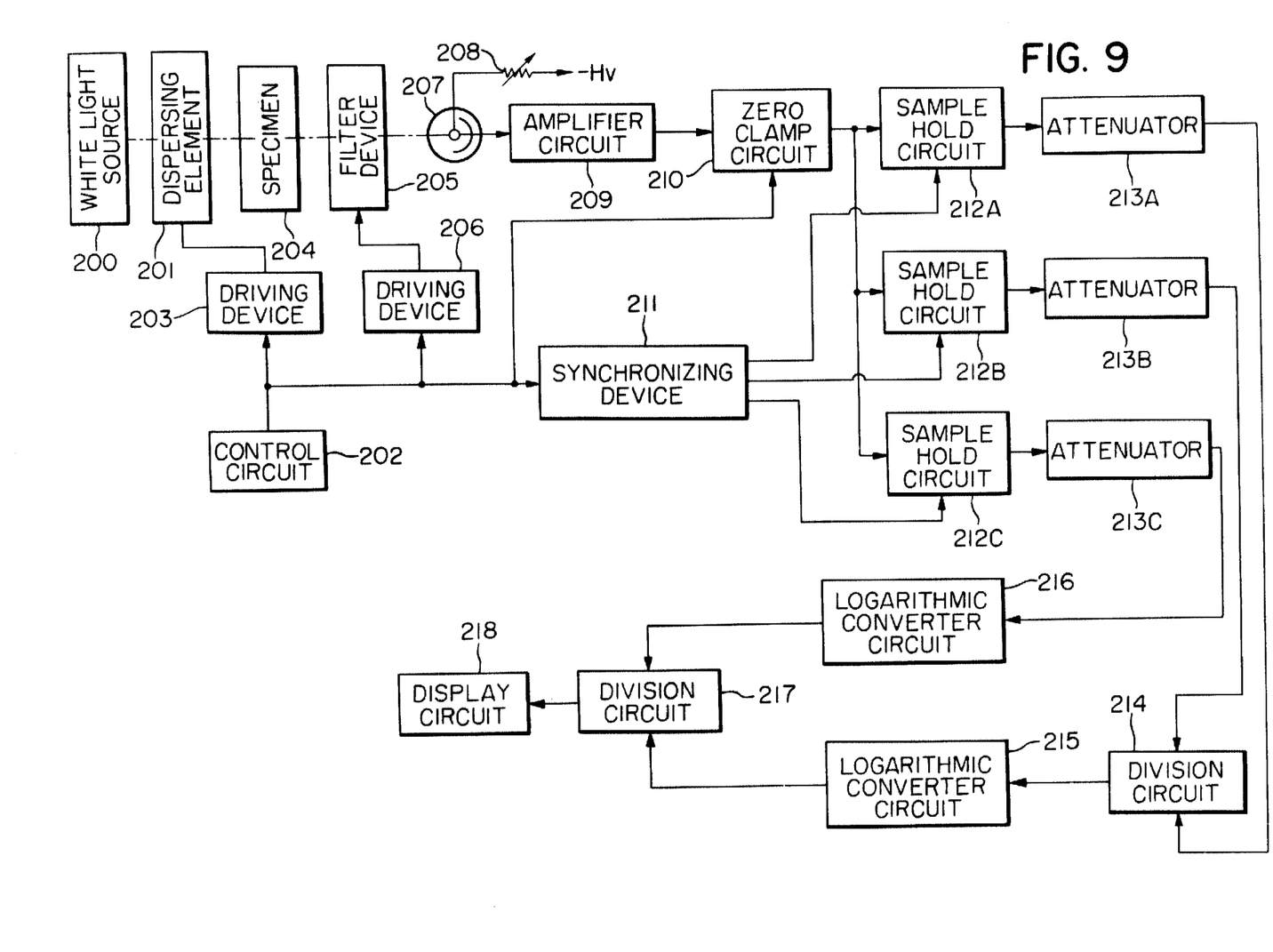
FIG. 9 shows another embodiment of the apparatus according to the present invention.

In the foregoing embodiment, data of three different wavelengths are obtained at a time, but the embodiment may be modified so that data of three wavelengths are time-sequentially obtained. Such modification is shown in FIG. 9.

Of the light beams from a white light source 200, a light beam of a predetermined wavelength is selected by a dispersing element 201. A control circuit 202 controls a driving device 203 so that, when a start switch, not shown, is closed, the dispersing element 201 selects the wavelengths in the vicinity of 450 nm, 570 nm and 700 nm in succession. The dispersing element 201 and the driving device 203 may be a mechanism comprising a grating and a sign bar or the like, or a mechanism for selectively inserting three wavelength selection filters in the light path. The present embodiment will be described with respect to the latter which is simpler. The light beam of a single wavelength emergent from the dispersing element 201 passes through a speciment 204, whereafter it passes through a filter device 205 to a photomultiplier 207. The filter device 205 has three ND filters corresponding to the wavelengths 450 nm, 570 nm and 700 nm, and a driving device 206 operates so that the ND filter corresponding to the wavelength selected by the dispersing element 201 is inserted in the light path in response to the control signal from the control circuit 202. The function of this ND filter is identical to that of the ND filter shown in FIG. 7. The light beam passed through the filter device is photoelectrically converted by a photomultiplier 207. The photomultiplier 207 is also similar to that shown in FIG. 7 in that its sensitivity is adjustable by adjusting a resistor 208. The photoelectric conversion signal is amplified by an amplifier circuit 209, whereafter it is subjected to dark current correction by a zero clamp circuit 210. Details of the zero clamp circuit 210 will later be described by reference to FIGS. 12, 13A, 13B and 13C. A synchronizing device 211 comprising a shift register or the like puts out a synchronizing signal for operating sample hold circuits 212A, 212B and 212C in succession in accordance with the signal from the control circuit 202. The outputs of the smaple hold circuits 212A, 212B and 212C are applied to attenuators 213A, 213B and 213C, respectively. The functions of the attenuators 213A, 213B and 213C will be described later. A devision circuit 214 divides the output of the attenuator 213A by the output of the attenuator 213B. The output of the division circuit 214 and the output of the attenuator 213C are logarithmically converted by logarithmic converter circuits 215 and 216, respectively. A division circuit 217 divides the output of the logarithmic converter circuit 216 by the output of the logarithmic converter circuit 215. That is, the outputs of the attenuators 213A, 213B and 213C respectively are signals $T_{450}$, $T_{700}$ and $T_{570}$ corresponding to the transmittivities of the corresponding wavelengths and therefore, the output of the division circuit 214 becomes $T_{450}/T_{700}$ and the outputs of the logarithmic converter circuits 215 and 216 become $\ln(T_{450}/T_{700})$ and $\ln T_{570}$, respectively. Accordingly, the output of the division circuit 217 becomes $$\frac{\ln T_{570}}{\ln \frac{T_{450}}{T_{700}}} = \frac{I_{570}}{I_{450} - I_{700}},$$

which is equation (1). Thus, it is possible to display the enzyme specific activity by a display circuit 218 to which the output of the division circuit 217 is applied.

Figure 10:
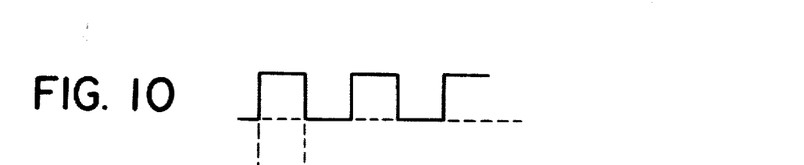
FIG. 10 shows the output waveform of a control circuit 202.
Figure 11A:
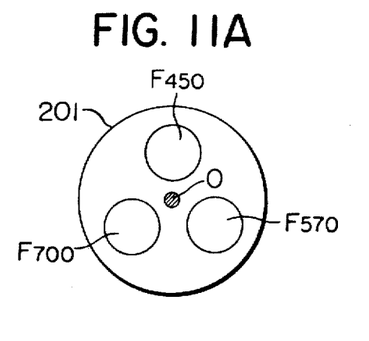
FIG. 11A shows a specific example of the dispersing element 201.
Figure 11B:
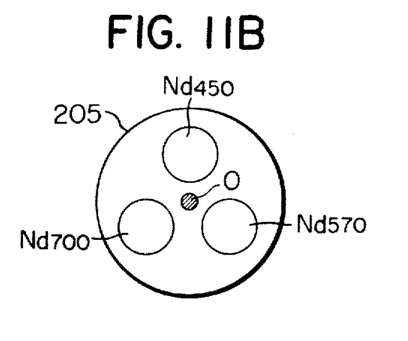
FIG. 11B shows a specific example of the filter device 205.

Operations of various parts of FIG. 9 will now be described. When a start switch, not shown, is closed, the control circuit 202 puts out a drive pulse of a predetermined period as shown in FIG. 10A. Driving devices 203 and 206 each comprise a stepping motor, for example, and secured to the rotary shafts of these motors are the rotary shafts 0 of discs having wavelength selection filters $F_{450}$, $F_{570}$, $F_{700}$ and ND filters $Nd_{450}$, $Nd_{570}$, $Nd_{700}$, respectively, as shown in FIGS. 11A and 11B. Accordingly, the aforementioned stepping motors are designed so that they rotate through 120° each time a pulse is applied thereto and therefore, they may be driven with correspondence taken between the wavelength selection filters and the Nd filters by the initial setting, as already described.

Figure 12:
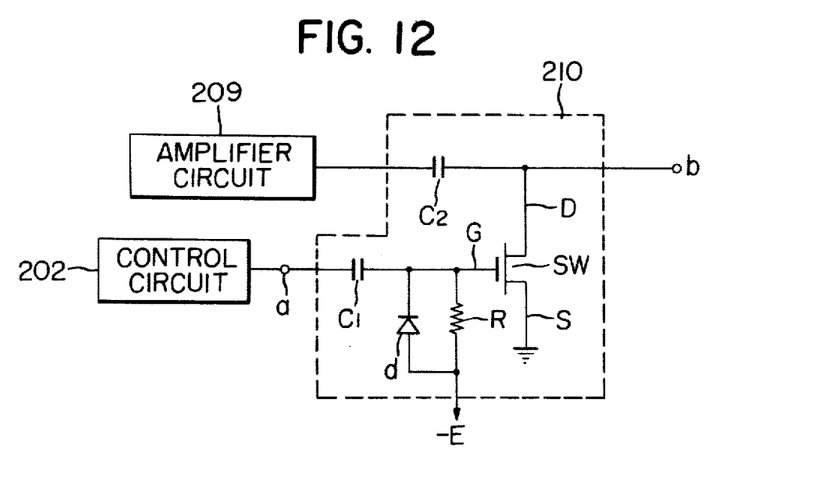
FIG. 12 shows a specific example of the zero clamp circuit 210.
Figure 13A:
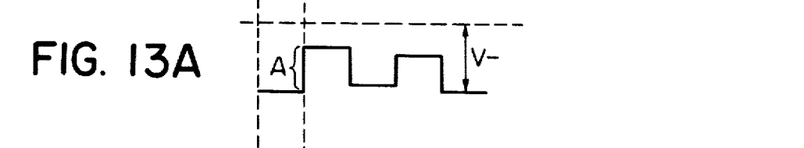
FIGS. 13A and 13B are graphs illustrating the operation of the zero clamp circuit.
Figure 13B:
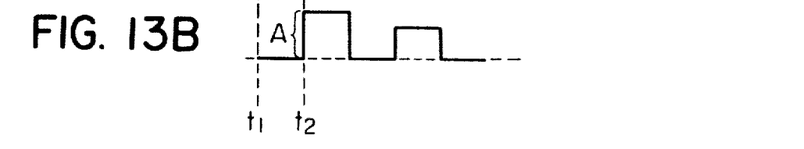

To the zero clamp circuit 210, details of which are shown in FIG. 12, a signal as shown in FIG. 13A is appied from an amplifier 209. Level V- is a voltage containing a DC error component such as dark current. The driving pulse from the control circuit 202 (FIG. 10) is applied from a control input terminal a. Connected to the gate G of an electronic switch SW comprising an FET is a negative power source −E through the other end of a capacitor C₁ having one end connected to the inptu terminal a, a reversely connected diode d and a resistor R. Also, the other end of a capacitor C₂ having one end connected to the amplifier 209 is connected the drain D of the switch SW and the output terminal b of the zero clamp circuit 210. The source S of the switch SW is grounded. Accordingly, when the driving pulse (FIG. 10) is applied from the control circuit 202, the switch SW is closed at the moment (t₁) of rising thereof to render the output terminal b to zero potential. Next, when signal is applied from the amplifier 209 at time t₂, a signal of level A as shown in FIG. 13B is provided at the output terminal b in spite of the level of the applied signal being (−V+A). By so passing the output of the amplifier 209 to the zero clamp circuit 210, the error component resulting from the dark current of the photomultiplier 207 may be removed.

Figure 14A:
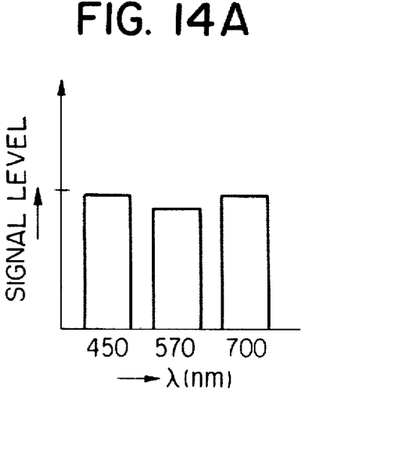
FIGS. 14A and 14B illustrate the actions of attenuators 213A–213C in the apparatus of FIG. 9.
Figure 14B:
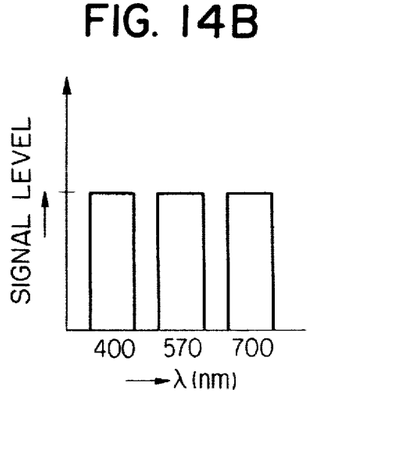

The functions of the attenuators 213A, 213B and 213C are as follows. In the embodiment of FIG. 7, there have been provided three detectors, namely, photomultipliers 105A, 105B and 105C corresponding to three wavelengths and so, it has been possible to effect fine adjustment of sensitivity. However, in the embodiment of FIG. 9, only one photomultiplier is used and so, even if adjustment of the sensitivity of the photomultiplier 207 is effected after the quantity of light incident on the photomultiplier 207 has been adjusted by the Nd filters Nd₄₅₀, Nd₅₇₀ and Nd₇₀₀ (see FIG. 11B) when the specimen 204 is not present in the light path, the outputs of three wavelengths are not always in accord with one another as shown in FIG. 14A. Attenuators 213A, 213B and 213C are provided to correct such discord and by adjusting them, the outputs thereof become regular in level as shown in FIG. 14B.

As has hitherto been described, according to the inventive method of measuring the specific activity of dehydrogenases and the apparatus therefor, it is possible to know localization of dehydrogenases in tissue flake as well as the specific activity of dehydrogenases and thus, is possible to effect the determination of dehydrogenases.

We claim:

1. A method of measuring the specific activity of dehydrogenases by using a specimen prepared through a first procedure of causing dehydrogenases in tissue flake to be measured to be reacted with a substrate for a predetermined time and dyeing the same with tetrazolium salt and a second procedure of dyeing the protein in said flake with naphthol yellows, the improvement comprising:
providing a third procedure of washing the enzyme-dyed flake with alcohol for a predetermined time after said first procedure, microphotometering a specimen prepared through said first, second and third procedures, by the use of three predetermined wavelengths in the vicinity of 450 nm, 570 nm and 700 nm to obtain the degree of light absorption, I, at each of said predetermined wavelengths, and applying said values to the formula $$I_{570}/I_{450} - I_{700}$$

to thereby obtain said specific activity, and measuring the specific activity of the dehydrogenases from data obtained corresponding to the respective wavelengths.

2. A method according to claim 1, wherein said third procedure is carried out between said first and said second procedure.

3. A method according to claim 2, wherein the alcohol used in said third procedure is monatomic alcohol.

4. A method according to claim 3, wherein said monatomic alcohol is ethanol.

5. An apparatus for measuring the specific activity of dehydrogenases by using a specimen prepared through a first procedure of causing dehydrogenases in tissue flake to be measured to be reacted with a substrate for a predetermined time and dyeing the same with tetrazolium salt, a second procedure of dyeing the protein of said flake with naphthol yellows and a third procedure of washing the enzyme-dyed flake with alcohol for a predetermined time after said first procedure, said apparatus including:

(a) a microphotometer capable of microphotometry by three predetermined wavelengths in the vicinity of 450 nm, 570 nm and 700 nm; said microphotometer having:
a white light source;
an optical system for condensing the light beam from said light source on a predetermined region of said specimen;
a light path splitting device for splitting the light beam passed through said specimen into a first, a second and a third light path;
first, second and third filter means disposed in said three light paths, respectively;
said filter means being capable of passing therethrough only wavelengths in the vicinity of 450 nm, 570 nm and 700 nm;
first, second and third photoelectric converter means corresponding to said three filter means, respectively, and for receiving the light beams passed through said three filter means; and
an optical system for condensing the light beams passed through said filter means on said photoelectric converter means;

(b) processing means having at least a first, a second and a third processing circuit provided corresponding to said three wavelengths, respectively;

(c) control means for distributing the metering outputs corresponding to said three wavelengths to said three processing circuits, said control means being a line for connecting said first, second and third photoelectric converter means to the corresponding first, second and third processing circuits; and (d) an operational device for effecting a predetermined operation between the output signals of said three processing circuits.

6. An apparatus according to claim 5, wherein said processing circuits have a first, a second and a third amplifier circuit for amplifying the outputs of said first, second and third photoelectric converter means, respectively, and a first, a second and a third logarithmic converter circuit for logarithmically converting the outputs of said first, second and third amplifier circuits, respectively, and said operational circuit includes a subtraction circuit for subtracting the output of said third logarithmic converter circuit from the output of said first logarithmic converter circuit, and a division circuit for dividing the output of said second logarithmic converter circuit by the output of said subtraction circuit.

7. An apparatus according to claim 5, wherein said microphotometer has means for inserting density filters into said first, second and third light paths, respectively.

8. An apparatus for measuring the specific activity of dehydrogenases by using a specimen prepared through a first procedure of causing dehydrogenases in tissue flake to be measured to be reacted with a substrate for a predetermined time and dyeing the same with tetrazolium salt, a second procedure of dyeing the protein of said flake with naphtol yellows and a third procedure of washing the enzyme dyed flake with alcohol for a predetermined time after said first procedure, said apparatus including:
 (a) a microphotometer capable of microphotometry by three predetermined wavelengths in the vicinity of 450 nm, 570 nm and 700 nm, said microphotometer having:
  a white light source;
  an optical system for condensing the light beam from said light source on a predetermined region of said specimen;
  photoelectric converter means for receiving the light beam passed through said speciman;
  an optical system for condensing the light beam from said specimen on said converter means; and
  a dispersing element provided in the light path between said light source and said photoelectric converter means, said dispersing element being capable of selectively emitting light beams in the vicinity of wavelengths 450 nm, 570 nm and 700 nm;
 (b) processing means having at least a first, a second and a third processing circuit provided corresponding to said three wavelengths, respectively;
 (c) control means for distributing the metering outputs corresponding to said three wavelengths to said three processing circuits; and
 (d) an operational device for effecting a predetermined operation between the output signals of said three processing circuits;
wherein said control means is operable to apply the output of said photoelectric converter means to the processing circuit corresponding to the wavelength selected by said dispersing element.

9. A method of measuring the specific activity of dehydrogenases by using a specimen prepared through a first procedure of causing dehydrogenases in tissue flake to be measured to be reacted with a substrate for a predetermined time and dyeing the same with tetrazolium salt and a second procedure of dyeing the protein in said flake with naphthol yellows, the improvement comprising:
 providing a third procedure of washing the enzyme-dyed flake with alcohol for a predetermined time after said first procedure, microphotometering a specimen prepared through said first, second, third procedures, by the use of three predetermined wavelengths in the vicinity of 450 nm, 570 nm, and 700 nm to obtain the degree of light transmittivity T, at each of said predetermined wavelengths, and applying said value of T to the formula $$\frac{\ln T_{570}}{\ln \frac{T_{450}}{T_{700}}}$$

to thereby obtain said specific activity, and measuring the specific activity of the dehydrogenases from data obtained corresponding to the respective wavelengths.

* * * * *